United States Patent [19]

Reist

[11] Patent Number: 5,424,315

[45] Date of Patent: Jun. 13, 1995

[54] BENZOTHIOPHEN ANALOGS AS ANTIVIRAL AGENTS

[75] Inventor: Elmer J. Reist, Menlo Park, Calif.

[73] Assignee: SRI International, Menlo Park, Calif.

[21] Appl. No.: 101,371

[22] Filed: Aug. 2, 1993

[51] Int. Cl.[6] .................. A61K 31/435; C07D 495/06
[52] U.S. Cl. .................... 514/285; 514/337; 546/62; 546/274
[58] Field of Search ............ 546/62; 514/285

[56] References Cited

U.S. PATENT DOCUMENTS

| | | | |
|---|---|---|---|
| 3,933,827 | 1/1976 | Brossi et al. | 546/70 |
| 4,018,780 | 4/1977 | Lappi et al. | 546/62 |
| 4,045,565 | 8/1977 | Le Pecq et al. | 546/70 |
| 4,310,667 | 1/1982 | Le Pecq et al. | 546/70 |
| 4,334,070 | 6/1982 | Berger et al. | 546/70 |
| 4,483,989 | 11/1984 | Le Pecq et al. | 546/70 |
| 4,851,417 | 7/1989 | Archer | 514/285 |
| 4,897,398 | 1/1990 | Gros et al. | 514/284 |

OTHER PUBLICATIONS

Shafiee et al. CA 84 (25): 180104C, 1976.
Shafiee et al. *Photochemical synthesis of [1]benzothieno[3,2-h]isoquinoline* (1976) *J. Heterocyclic Chem.* 13:141–144.
Duke et al. *In vitro and in vivo activities of phosphate derivatives of 9-(1,3-dihydroxy-2-propoxymethyl)guanine against cytomegaloviruses.* (1986) *Antiviral Res.* 6:299–308.
Cheng et al. *Unique spectrum of activity of 9-[(1,3-dihydroxy-2-propoxy)methyl]guanine against herpesviruses in Vitro and its mode of action against herpes simplex virus type 1.* (1983) *Proc. Natl. Acad. Sci. USA* 80:2767–2770.

Primary Examiner—Jane T. Fan
Attorney, Agent, or Firm—Reed & Robins

[57] ABSTRACT

Benzothiophene analogs useful to treat herpes viral infections, particularly cytomegalovirus, are provided. These antiviral agents have the structural formula (I)

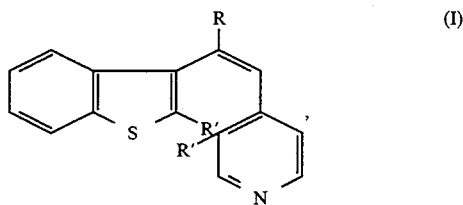

wherein R and R[1] are as defined herein, and may be in free base or acid addition salt form. Pharmaceutical compositions are provided containing the antiviral agents, as are methods of treating herpes-infected individuals.

11 Claims, No Drawings

BENZOTHIOPHEN ANALOGS AS ANTIVIRAL AGENTS

ACKNOWLEDGEMENT OF GOVERNMENT SUPPORT

This invention was made, in whole or in part, with U.S. Government support under a contract from the National Institutes of Health.

TECHNICAL FIELD

This invention relates generally to the field of antiviral agents, and more particularly relates to novel benzothiophene analogs for treating herpes viral infections, particularly cytomegalovirus ("CMV"). The invention additionally relates to pharmaceutical compositions containing the antiviral agents and to methods of treating individuals who are infected with a herpes viral infection.

BACKGROUND

There are six known herpes-type viruses which affect human beings: herpes zoster (chicken pox), herpes simplex virus I & II (cold sores and genital herpes), cytomegalovirus (cytomegalic inclusion disease), Epstein-Barr virus (mononucleosis), and the recently isolated Herpes VI virus. The herpes viruses are medium-sized viruses containing double-stranded DNA, with a nucleocapsid about 100 nm in diameter surrounded by a lipid-containing envelope. The virion is 150–200 nm in diameter and permits latent infections which last for the life span of the host even when antibodies are present.

The present invention is specifically directed to novel compounds which have been found useful for treating cytomegalovirus. Human cytomegalovirus is a ubiquitous agent in human populations. Infections are generally asymptomatic, but there can be serious medical manifestations of the disease in immunocompromised individuals (e.g., transplant recipients and AIDS patients) and in congenitally infected newborns. Present drug therapies for treating CMV are not always effective, insofar as the virus may be resistant to the commonly used nucleoside-type pharmaceuticals such as ganciclovir and foscarnet. Additionally, the former drug, when combined with the AIDS drug azidothymidine ("AZT"), a dideoxynucleoside, can give rise to synergistic toxicity, and thus is severely limited in its usefulness for treating CMV in AIDS patients.

The antiviral agents of the invention are novel nonnucleoside compounds which will be described in detail hereinbelow. Because these compounds are not nucleosides or nucleoside analogs, they operate by an entirely different mechanism of action than do the compounds of the prior art, and do not result in the disadvantages associated with those compounds.

Several references are of interest which relate to benzothiophene analogs as pharmaceutical agents. These include U.S. Pat. Nos. 4,045,565, 4,310,667 and 4,483,989 to Le Pecq et al., 4,851,417 to Archer, and U.S. Pat. No. 4,897,398 to Gros et al. All of the aforementioned patents relate to benzothiophene analogs in the form of 9-hydroxy ellipticine or derivatives thereof, as anti-cancer agents. U.S. Pat. No. 3,933,827 to Brossi et al. and 4,334,070 to Berger et al. describe similar compounds as cytostatic agents and antipsychotic drugs, respectively. These references do not, however, suggest or disclose the newly discovered compounds described herein, nor do they suggest that benzothiophene or ellipticene derivatives would be useful to treat herpes viruses in general, or CMV in particular.

SUMMARY OF THE INVENTION

It is accordingly a primary object of the invention to provide novel antiviral agents useful to treat herpes viral infections.

It is another object of the invention to provide such antiviral agents which are specifically useful to treat cytomegalovirus.

It is still another object of the invention to provide such antiviral agents in the form of novel benzothiophene analogs.

It is a further object of the invention to provide methods and pharmaceutical compositions for treating herpes viral infections.

It is still a further object of the invention to provide methods and pharmaceutical compositions for treating cytomegalovirus using the antiviral agents of the invention.

Additional objects, advantages and novel features of the invention will be set forth in part in the description which follows, and in part will become apparent to those skilled in the art upon examination of the following, or may be learned by practice of the invention.

In one aspect, then, the invention relates to antiviral agents having the structural formula (I)

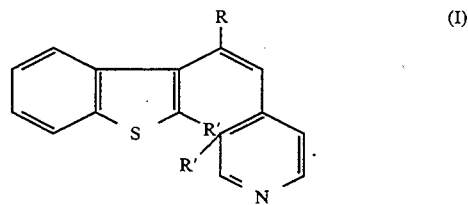

In Formula (I), the R' are hydrogen or are linked together to form a single covalent bond, and R is selected from the group consisting of:
—COOR$^1$ where R$^1$ is H, lower alkyl or phenyl;
—CONHR$^1$; and
—NHR$^2$ where R$^2$ is selected from the group consisting of H, lower alkyl, and —COOR$^3$ where R$^3$ is lower alkyl or trifluoromethyl. These planar compounds represent a new class of nonnucleoside compounds which show significant antiviral activity against herpes viruses, particularly against cytomegalovirus.

In another aspect of the invention, compounds having the structural Formula (I), but wherein R is —CN, are provided as useful starting materials and intermediates in the synthesis of the antiviral compounds of the invention.

In other aspects of the invention, pharmaceutical compositions are provided which contain one or more of the aforementioned benzothiophene analogs in combination with a pharmaceutically acceptable excipient. These compositions may be administered to an herpes-infected individual, preferably a cytomegalovirus-infected individual, to alleviate the symptoms caused by the virus.

DETAILED DESCRIPTION OF THE INVENTION

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an antiviral agent" includes mixtures of antiviral agents, reference to "a pharmaceutical carrier" includes mixtures of two or more such carriers, and the like.

By the term "alkyl" as used herein is meant a branched or unbranched saturated hydrocarbon chain of 1 to 20 carbon atoms. The term "lower alkyl" intends an alkyl group of 1 to 6 carbon atoms such as methyl, ethyl, n-propyl, isopropyl, t-butyl, and the like.

"Optional" or "optionally" means that the subsequently described circumstance may or may not occur, and that the description includes instances where said circumstance occurs and instances where it does not. For example, the phrase "optional covalent bond" means that a covalent bond may or may not be present and that the description includes both the instance when the covalent bond is present and the instance when the covalent bond is not present.

By the phrase "herpes viral infection" is meant infection with any one of the known herpes viruses, i.e., herpes simplex types I or II, cytomegalovirus, herpes zoster, Epstein-Barr virus, or herpes VI. However, as noted earlier herein, the compounds of the invention are particularly useful in treating cytomegalovirus.

By the term "effective amount" of an antiviral agent is meant a nontoxic but sufficient amount of the agent to provide the desired treatment of viral infection. As will be pointed out below, the exact amount required will vary from subject to subject, depending on the species, age, and general condition of the subject, the severity of the infection, the particular antiviral agent and its mode of administration, and the like. Thus, it is not possible to specify an exact "effective amount." However, an appropriate effective amount may be determined by one of ordinary skill in the art using only routine experimentation.

By "pharmaceutically acceptable" is meant a material which is not biologically or otherwise undesirable, i.e., the material may be administered to an infected individual along with the selected antiviral agent without causing any undesirable biological effects or interacting in a deleterious manner with any of the other components of the pharmaceutical composition in which it is contained.

The benzothiophene analogs with which the invention is concerned have the structural formula (I), above, with R and R' as defined earlier. A first group of specific and preferred compounds within the general class of compounds defined by formula (I) are wherein the R' are linked to form a single covalent bond, and wherein if R is —NHR², it is preferably —NH₂, —NHCOOCH₃, or —NHCOF₃, and if R is —COOR¹, it is preferably —COOCH₃. A second compound which is a preferred drug within the scope of formula (I) is wherein the R' are both hydrogen and R is —CN. These compounds may be illustrated as follows:

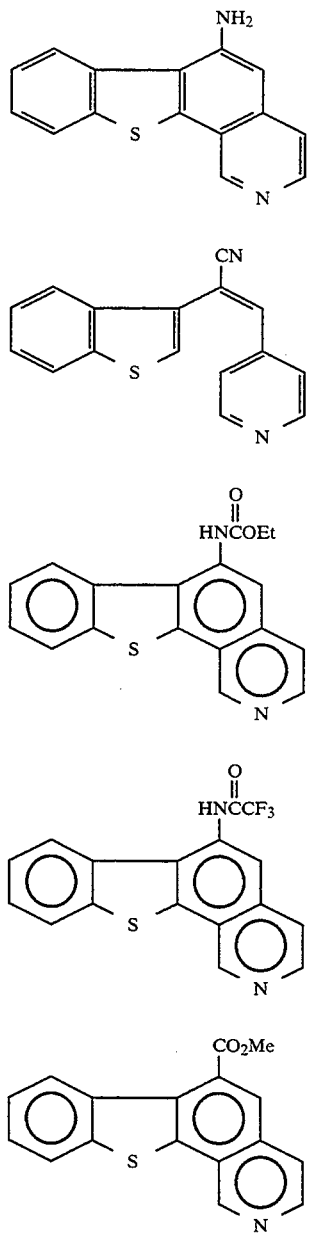

These compounds are readily synthesized as illustrated in Scheme 1, and as described in detail in the examples below. Briefly, 6-cyanobenzothieno [3,2-h] isoquinoline (or a derivative thereof encompassed by the generic structure of Formula (I)) is prepared from 3-chloromethylthianaphthene, followed by whatever conversions may be desired at the 6- position, e.g., preparation of 6-amino, 6-amide, 6-carboxyl, or 6-ester analogs, as described in Examples 1–7. Ring closure—between the two heterocyclic moieties of the molecule—may also be effected, if desired (see Example 1).

Reaction Scheme 1
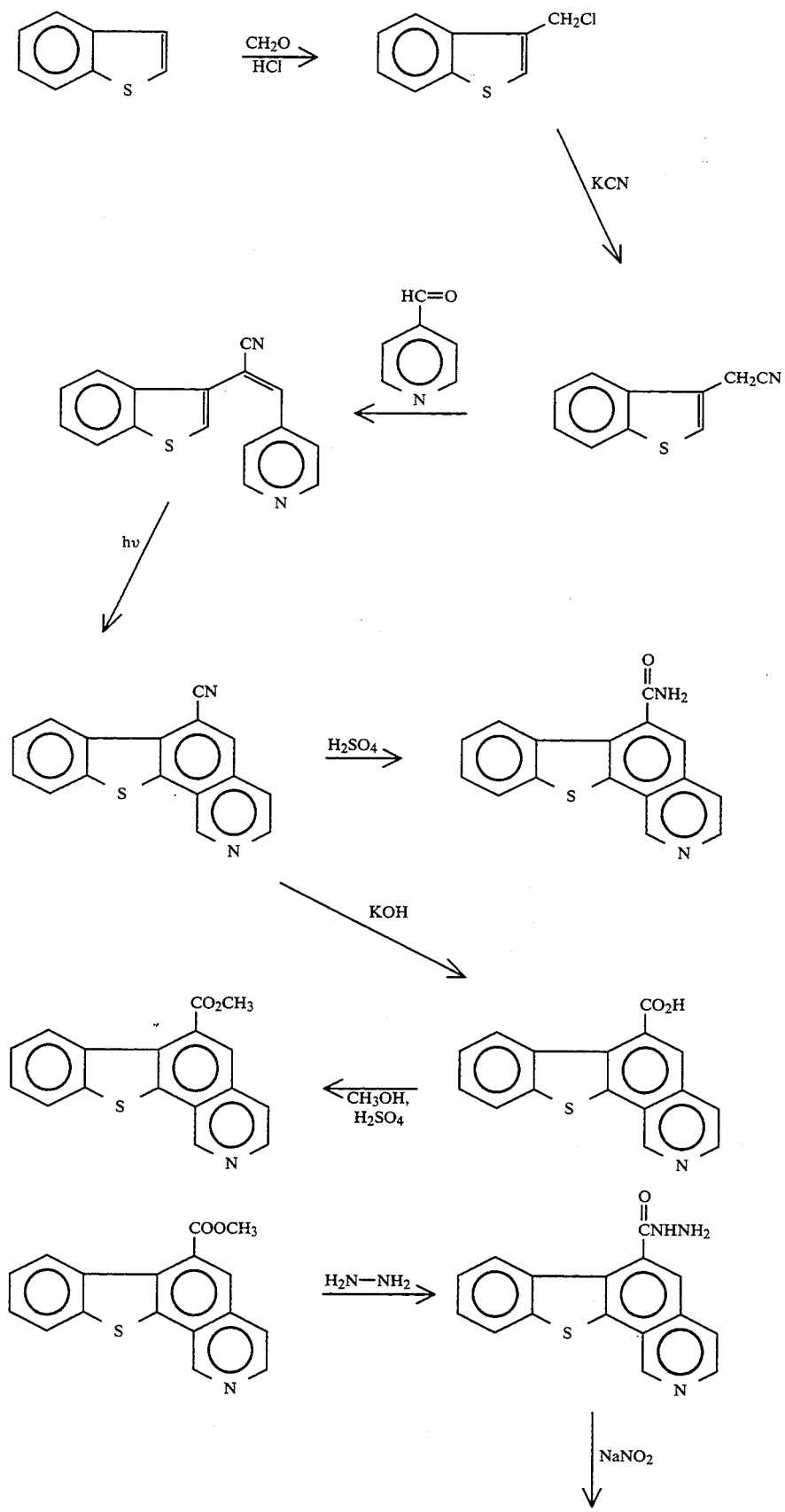

Reaction Scheme 1 -continued

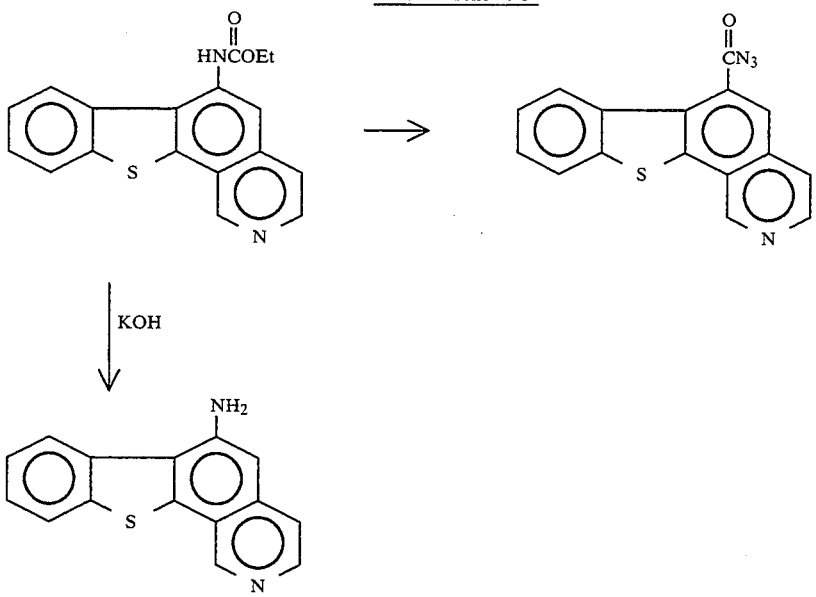

The compounds may also be converted to their acid addition salts which retain the biological effectiveness and properties of the free bases, and such compounds are also within the scope of the present invention. Acid addition salts are prepared by reacting a compound of the invention with an organic or inorganic acid. Suitable acids include, for example, hydrochloric acid, hydrobromic acid, sulfuric acid, acetic acid, propionic acid, glycolic acid, oxalic acid, malonic acid, succinic acid, tartaric acid, cinnamic acid, methane sulfonic acid, p-toluene sulfonic acid, salicylic acid, and the like. The free base is dissolved in a polar organic solvent such as methanol or ethanol and the acid is added at a temperature of about 0° C. to about 100° C., preferably at about room temperature. The resulting salt either precipitates or may be brought out of solution by addition of a less polar solvent. The acid addition salt is reconverted to the free base by treating with suitable base.

As noted earlier herein, the compounds of the invention defined by structural formula I, including the physiologically acceptable salts thereof, have antiviral activity against herpes viral infections and against cytomegalovirus in particular. The compounds may be conveniently formulated into pharmaceutical preparations composed of one or more of the compounds in association with a pharmaceutically acceptable carrier. *Remington's Pharmaceutical Sciences*, latest edition, by E. W. Martin (Mack Publ. Co., Easton Penna.) discloses typical carriers and methods of preparation known in the art.

The compounds may be administered topically, orally, parenterally (e.g., intravenously), by intramuscular injection, or by intraperitoneal injection, or the like, depending on the nature of the herpes viral infection being treated. For internal infections, the compositions are administered orally or parenterally at dose levels of about 0.1 to 300 mg/kg, preferably 1.0 to 30 mg/kg of mammal body weight, and can be used in humans in a unit dosage form administered one to four times daily in the amount of 1 to 250 mg per unit dose.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Alternatively, for topical infections, e.g., mouth and skin, the compositions are preferably applied to the infected part of the body of the patient topically as an ointment, cream, aerosol or powder, preferably as an ointment or cream. The compounds may be presented in an ointment, for instance with a water-soluble ointment base, or in a cream, for instance with an oil in water cream base in a concentration of from about 0.01 to 10% preferably 0.1 to 7%, most preferably about 0.5% w/w. Additionally, viral infections of the eye, such as Herpetic keratitis, may be treated by use of a sustained release drug delivery system as is known in the art.

The exact regimen for administration of the compounds and compositions disclosed herein will necessarily be dependent upon the needs of the individual subject being treated, the type of treatment and the judgment of the attending practitioner.

EXPERIMENTAL

The following examples are put forth so as to provide those of ordinary skill in the art with a complete disclosure and description of how the antiviral agents claimed herein are made and evaluated, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

Examples 1–7 describe preparation of various compounds encompassed by structural formula I. Example 8 summarizes the testing which was carried out to evaluate antiviral activity.

EXAMPLE 1

Preparation of 6-Cyanobenzothieno-[3,2-h]Isoquinoline (4)

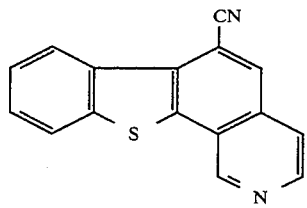

A. Preparation of 3-cyanomethylthianaphthene (2):

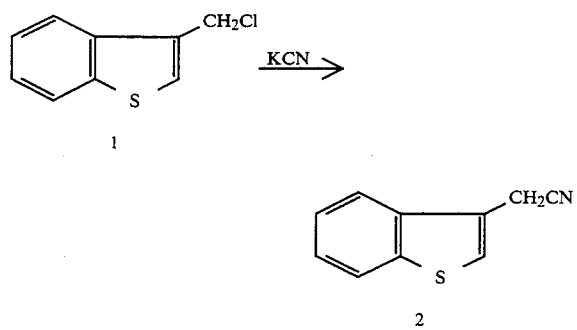

To a mixture of 4.9 g KCN in 20 mL DMSO was slowly added 12.47 g (68.5 mM) 3-chloromethyl-thianaphthene. A red color developed. The reaction was stirred at room temperature overnight, and appeared heterogeneous. The reaction mixture was then poured into 200 mL cold water. A red oil separated and partially solidified. The mixture was extracted four times with a total of 200 ml ether; the ether solution was washed with saturated NaCl solution, dried and concentrated, leaving a light brown solid. This product was then recrystallized from a mixture of isopropanol and petroleum ether to yield 10.2 g of a light brown solid, m.p. approximately 63° C.–65° C. This product was then again recrystallized, twice, from a mixture of benzene and petroleum ether, to yield 6.4 g of product 2 having a melting point 64.5° C.–66° C.

B. Preparation of 3-[α-cyano-β-(4-pyridyl)vinyl]-thianaphthene (3):

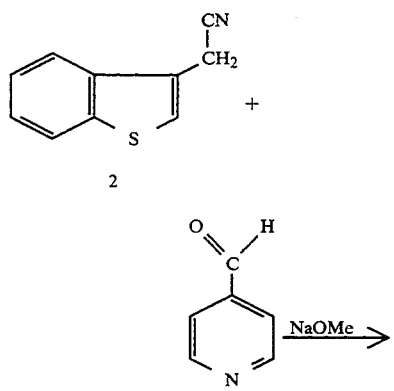

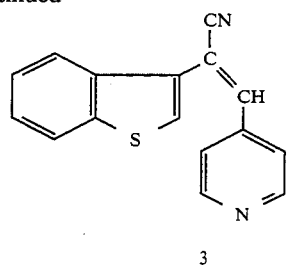

A solution of 173 mg (1 mM) of 3-cyanmethyl-thianaphthene (2) and 126 mg (1.17 mM) pyridine 4-carboxaldehyde in about 1 ml warm ethanol was treated with 2 drops of 1 M NaOH and allowed to stand at room temperature. After half an hour, a pale yellow solid began to separate. The reaction mixture was then chilled in ice, diluted with 95% ethanol, and filtered. The product was collected and washed with cold 95% ethanol to provide 10 mg of a pale yellow solid, m.p. 140° C.–145° C. This initial product was then recrystallized from 95% ethanol, followed by recrystallization from petroleum ether, to provide 60 mg product, m.p. 146.5° C.–148° C. The product was characterized by NMR and mass spectrometry as compound 3.

C. Preparation of 6-cyanobenzothieno[3,2-h]isoquinoline (4):

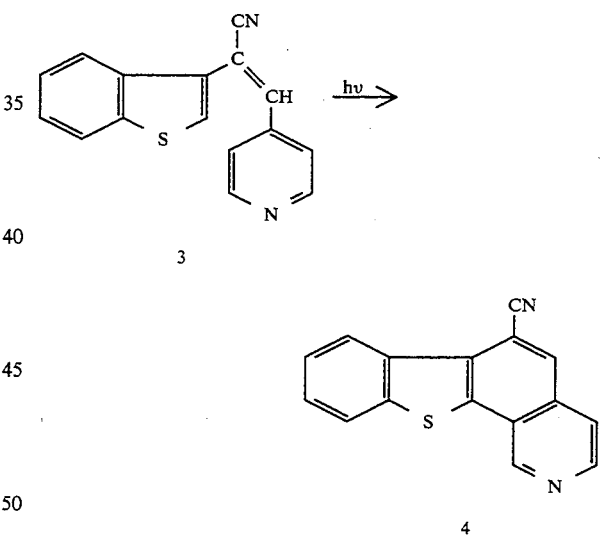

250 mg of 3-[α-cyano-β-(4-pyridyl)vinyl]thianaphthene (3) dissolved in 40 ml benzene and 160 ml t-butanol was irradiated (450 watt Hg vapor lamp) through quartz walls, while the reaction mixture was stirred and had air bubbled therethrough. The mixture was allowed to stand overnight. The residue was then extracted twice with boiling $CHCl_3$. The extracts were combined, and evaporated to yield a yellow solid residue, 215 mg. This product was then dissolved in 50 ml hot methanol, filtered and concentrated, to give a sticky brown residue, 60 mg. This residue was then crystallized from $CHCl_3$/acetone to yield 26 mg of a tan, crystalline solid, m.p. 288° C.–290° C., characterized as compound 4 by infrared spectroscopy and mass spectrometry.

EXAMPLE 2

Preparation of Benzothieno[3,2h]Isoquinoline-6-Carboxylic Acid Amide (5)

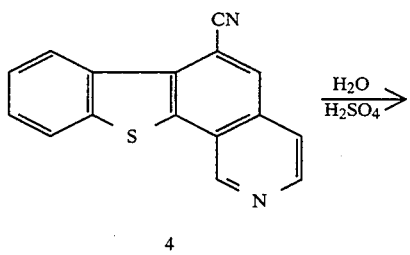

4

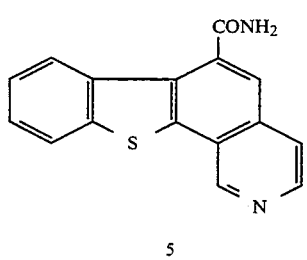

5

Two hundred mg of 6-cyanobenzothieno[3,2-h]isoquinoline (4), prepared in the preceding Example, was mixed with a solution of 2 ml water and 3 ml concentrated sulfuric acid. The reaction mixture was heated at 110° C.–120° C., and gave rise to a yellowish brown solution. After heating for approximately 5 hr, when TLC indicated the absence of starting material, the reaction mixture was poured onto 40 ml ice and water. The yellow solution thus obtained was made alkaline (to a pH of about 8) with concentrated ammonium hydroxide. The gray flocculent solid that precipitated was collected and washed with water to yield 130 mg dried product. This material was recrystallized from 75 ml CHCl$_3$, to give 85 mg of a white solid, m.p. 295° C.–302° C., characterized as compound 5 by I.R. and mass spectrometry.

EXAMPLE 3

Preparation of 6-Carboxybenzothieno[3,2-h]Isoquinoline (6)

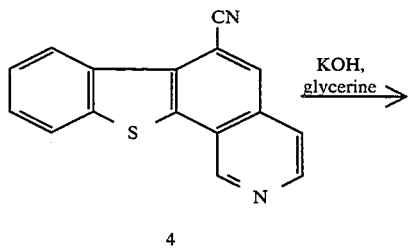

4

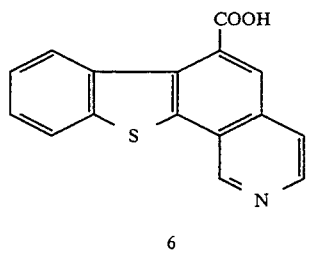

6

One hundred thirty mg (0.5 mM) of 6-cyanobenzothieno[3,2-h]isoquinoline (4), prepared in Example 1, was suspended in a hot solution of 168 mg (3 mM) KOH in 1 ml glycerine. The reaction mixture was stirred and heated at 160° C.–170° C. overnight. The resulting yellow solution was cooled, diluted with water and made slightly acidic with glacial acetic acid. A yellow precipitate was collected, washed with water, and air dried to yield 120 mg of product. This initial product was recrystallized from a mixture of DMSO and water to give 78 mg product, mp greater than about 305° C. This then was dried at 80° C./0.2 mm overnight, and characterized as compound 6 using I.R. and mass spectrometry.

EXAMPLE 4

Preparation of 6-Carbomethoxybenzothieno[3,2-h]Isoquinoline (7)

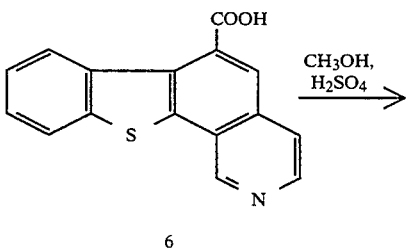

6

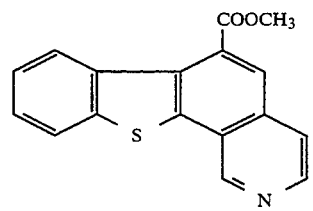

7

1.02 g of the acid 6 was refluxed in 100 ml of a methanol:conc. H$_2$SO$_4$ (4:1) mixture. The acid quickly dissolved. The reaction was heated at reflux for 5–6 hours. The resulting yellow solution was filtered, cooled, slowly diluted with 300 ml H$_2$O, and made alkaline with approximately 20 ml NH$_4$OH. A pale yellow solid separated and was air dried, m.p. 174°–176° C. This product was recrystallized three times from methanol to yield a white crystalline solid, m.p. 175.5°–177° C., which was characterized via I.R. and mass spectrometry as compound 7.

EXAMPLE 5

Preparation of Benzothieno[3,2-h]Isoquinoline-6-Carboxylic Acid Hydrazide (8)

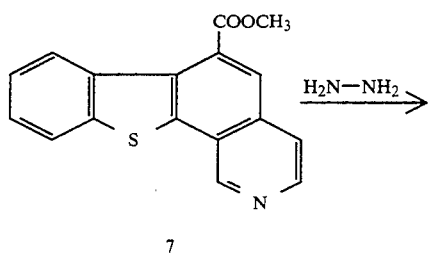

7

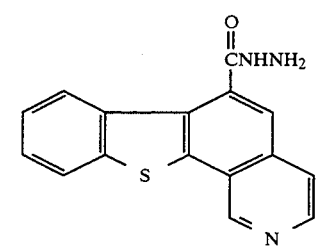

8

A solution of 0.2 g (0.68 mM) of the methyl ester 7 prepared as in Example 4 in 20 ml ethanol and 5 ml 95% hydrazine was heated at reflux for approximately 6-7 hr. The reaction mixture was cooled and the resulting white solid was collected, washed with ethanol and air dried to yield 170 mg product, m.p. 285° C.–289° C. The initial product was then recrystallized twice from a mixture of DMF and water to yield a final product having an m.p. in the range of about 295° C.–299° C. The product was characterized as compound 8 using I.R. and mass spectrometry.

EXAMPLE 6

Preparation of 6-Carboethoxyaminobenzothieno-[3,2-h]Isoquinoline (9)

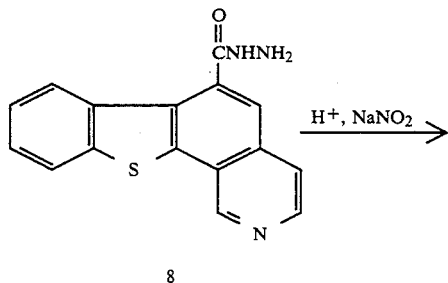

8

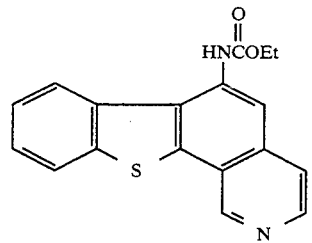

9

One hundred mg (0.34.mM) of the hydrazide 8 prepared in Example 5 was dissolved in 5 ml warm glacial acetic acid. The reaction mixture was cooled in ice and 1 ml water was added, followed by gradual addition of 50 mg (0.72 mM) NaNO$_2$ in 1 ml H$_2$O. A yellow solid slowly began to separate. The mixture was stirred in an ice bath for 30 minutes, at which point 25 ml water was added. A yellow solid was then collected, which was washed with water and then with ethanol. The slightly damp material was suspended in 15 ml ethanol and heated at reflux for 2-3 hr. The solution was then cooled and the product collected and recrystallized twice from ethanol. The resulting white crystalline solid begins to darken and melt at approximately 220° C., but does not completely melt. The product was characterized via I.R. and mass spectrometry as compound 9.

EXAMPLE 7

Preparation of 6-Aminobenzothieno [3,2 -h ]Isoquinoline (10)

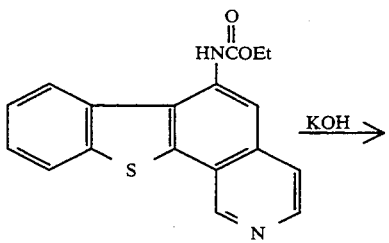

9

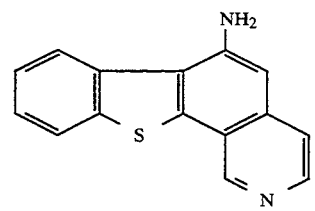

10

Two hundred mg (0.62 mM) of 6-carbethoxyaminobenzothieno[3,2-h]isoquinoline (9), prepared in the preceding Example, was added to a solution of 2 g KOH in 5 ml ethanol and 2 ml water. Two layers formed. The mixture was stirred and heated at reflux for approximately 2-3 hr. A yellow solid separated after about an hour, and was collected via filtration and air dried to give 160 mg product, m.p. 220° C.–225° C. This initial product was recrystallized twice from a mixture of DMF and water to provide 120 mg final product, m.p. 223.5° C.–224.5° C., which was then characterized via I.R. and mass spectrometry as compound 10.

EXAMPLE 8

The compounds prepared in the previous Examples were evaluated in vitro as antiviral agents against cytomegalovirus, as follows.

The herpes virus strain employed was Strain McCrae of type 1 herpes (thymidine kinase positive virus) (HSV-1TK+). This strain was prepared and titered in MA-104 cells and frozen at −90° C. until use. Also used were strain HF (HSV-1TK−), strain E194 (HSV-2), NJB strain (MCMV), and strain AD169 (HCMV).

Continuous passaged MRC-5 cells obtained from the American Type Culture Collection (Bethesda, Md.) were used for testing of herpes-type virus, with growth medium consisting of Minimum Essential Medium (MEM) supplemented with 0.1% $NaHCO_3$ and 50 µL gentamicin.

To a 96 well microtiter plate containing an established 24 hour monolayer of cells from which the medium has been decanted was added 0.1 mL of varying (one-half $log_{10}$) concentrations of test compound, which incubated on the cell 15 minutes, after which 0.1 mL of virus in a concentration of 320 cell culture 50% infectious doses ($CCID_{50}$)/0.1 mL was added. The plate was covered with plastic wrap and incubated at 37° C. The cells were examined microscopically after 72 hours for evidence of cytotoxicity and for viral cytopathic effect (CPE). Results are set forth in Table 1:

TABLE 1

| Compound | $CD_{50}$ | $ED_{50}$ | TI |
| --- | --- | --- | --- |
| 1 | >10 | 0.1 | >100 |
| 2 | >100 | 2.5 | >40 |
| 3 | >32 | <1 | >32 |
| 4 | 196 | <1 | >196 |
| 5 | 1.3 | 0.08 | 16 |

I claim:

1. A compound having the structural formula (I)

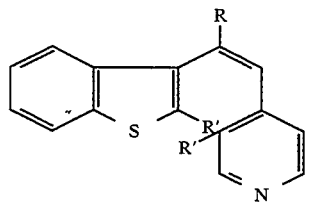

(I)

wherein:
the R' are linked together to form a single covalent bond; and
R is selected from the group consisting of
—$COOR^1$ where $R^1$ is H, lower alkyl or phenyl,
—$CONHR^1$, and
—$NHR^2$ where $R^2$ is selected from the group consisting of H, lower alkyl, and —$COOR^3$ where $R^3$ is lower alkyl or trifluoromethyl.

2. The compound of claim 1, wherein R is —$NHR^2$.

3. The compound of claim 2, wherein R is —$NH_2$.

4. The compound of claim 2, wherein R is —NHCOOCH$_3$.

5. The compound of claim 2, wherein R is —NHCOOCH$_2$CH$_3$.

6. The compound of claim 2, wherein R is —NHCOCF$_3$.

7. The compound of claim 1, wherein R is —$COOR^2$.

8. The compound of claim 7, wherein R is —COOCH$_3$.

9. A pharmaceutical composition for treating herpes viral infection which comprises, in combination with a pharmaceutically acceptable excipient, a compound having the structural formula (I):

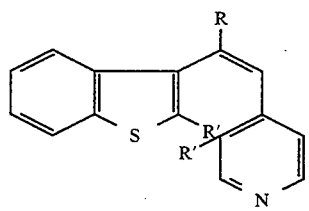

(I)

wherein:
the R' are linked together to form a single covalent bond; and
R is selected from the group consisting of
—$COOR^1$ where $R^1$ is H, lower alkyl or phenyl,
—$CONHR^1$, and
—$NHR^2$ where $R^2$ is selected from the group consisting of H, lower alkyl, and —$COOR^3$ where $R^3$ is lower alkyl or trifluoromethyl.

10. A pharmaceutical composition for treating herpes viral infection which comprises an effective amount of the compound of claim 2 in combination with a pharmaceutically acceptable excipient.

11. A pharmaceutical composition for treating herpes viral infection which comprises an effective amount of the compound of claim 7 in combination with a pharmaceutically acceptable excipient.

* * * * *